United States Patent [19]

Acton et al.

[11] Patent Number: 4,705,850

[45] Date of Patent: Nov. 10, 1987

[54] C-GLYCOSIDIC ADRIAMYCIN ANALOGS

[75] Inventors: Edward M. Acton, Menlo Park; Kenneth J. Ryan, Sunnyvale; Michael Tracy, Menlo Park, all of Calif.

[73] Assignee: SRI International, Menlo Park, Calif.

[21] Appl. No.: 674,175

[22] Filed: Nov. 23, 1984

Related U.S. Application Data

[63] Continuation-in-part of Ser. No. 664,524, Oct. 25, 1984, abandoned.

[51] Int. Cl.[4] .................. C07H 7/02; C07H 15/24
[52] U.S. Cl. ....................... 536/1.1; 536/18.7; 536/55.2; 536/55.3; 536/124
[58] Field of Search ............ 536/1.1, 124, 18.7, 536/55.2, 55.3

[56] References Cited

U.S. PATENT DOCUMENTS

| | | | |
|---|---|---|---|
| 2,746,956 | 5/1956 | Speier | 536/7.2 |
| 4,446,312 | 5/1984 | Noyori et al. | 536/1.1 |
| 4,464,529 | 8/1984 | Mosher et al. | 536/6.4 |

OTHER PUBLICATIONS

Acton, E. M. et al., *Tetrahedron Letters*, (1984) 25:5743-5746.
Acton, E. M. et al., *Carbohyde., Res.*, (1981) 97:235-245.
Chandler, M. et al., (1980), *J.C.S. Perkin I.*, 1007-1012.
Kozikowski, A. P. et al., (1983), *Tetra. Letters*, 24:1563-1566.
Lewis, M. D. et al., (1982), *J. Am. Chem. Soc.*, 104:4976-4978.

*Primary Examiner*—Ronald W. Griffin
*Attorney, Agent, or Firm*—Ciotti & Murashige, Irell & Manella

[57] ABSTRACT

Disclosed herein is a new procedure for preparing the C.1-2,4-pentadienyl derivatives of 2-deoxyhexopyranoses, as well as a new procedure for allylation of daunosamine. These methods are particularly useful for the preparation of intermediates in the synthesis of adriamycin C-glycosidic analogs which are useful antitumor agents. These methods provide the first enabling disclosure of methods to prepare these desired adriamycin and anthrocyclinone C-glycosidic analogs.

17 Claims, No Drawings

C-GLYCOSIDIC ADRIAMYCIN ANALOGS

ACKNOWLEDGEMENT OF GOVERNMENT SUPPORT

This work was supported by PHS Grant CA32250, awarded by the National Cancer Institute, DHHS.

CROSS-REFERENCE TO RELATED APPLICATIONS

This application is a continuation-in-part of U.S. application Ser. No. 664,524, filed Oct. 25, 1984 and now abandoned.

TECHNICAL FIELD

This invention concerns synthetic methods in the preparation of desired organic compounds. More particularly, the invention concerns general methods which can be used specifically for the preparation of intermediates in the synthesis of G-glycosidic adriamycin and ametantrone analogs which will have useful anti-tumor activity.

BACKGROUND ART

Among the plethora of chemotherapeutic agents in use at this time for the treatment of solid tumors, metastatic conditions, and leukemias, adriamycin and its analogs are among the most prominent. Adriamycin is a commercial name for doxorubicin, which is a polycyclic naphthacene-based glycoside of the deoxyamino sugar, daunosamine. A class of similar compounds, which are also glycosides of daunosamine, but which contain polycyclic systems related to anthracene, is represented by ametantrone and mitoxantrone. This class also has powerful anti-tumor activity.

It has been suggested that the C-glycoside analogs of these anti-tumor compounds might have some advantageous properties in connection with their therapeutic use. It is known that adriamycin and its analogs are inactivated by de-glycosidation. It is expected that though the C-glycoside analogs would be resistant to this degradation, as they are isosteric to compounds of known anti-tumor activity, they should be effective in analogous therapeutic ways. Acton, E. M., et. al, *Carbohydrate Research* (1981) 97:235-245 suggested a synthetic pathway for the preparation of such C-glycosidic analogs, but the reaction pathway suggested has since been shown not to yield the expected products. Therefore, although the goal was stated, the means for attaining it have not been available in the art.

The present invention provides a general means for obtaining essential intermediates in the production of the desired C-glycosides. It is also of general use in obtaining pentadienyl and acetaldehyde derivatives of 2-deoxypyranose sugars.

DISCLOSURE OF THE INVENTION

This invention enables the product of C.1 (2,4-pentadienyl)glycosides of a 2-deoxypyranose, and, in particular, these derivatives of daunosamine. The method is useful for preparing the acetaldehyde derivatives as well. The resulting pentadienyl derivatives are useful as intermediates because they can then be linked to appropriate polycyclic systems using a Diels-Alder reaction and converted to desired C-glycosidic adriamycin analogs using standard means known in the art. The acetaldehyde derivatives are useful as substrates for Wittig type reactions to obtain related pentadienyl derivatives.

Thus, the methods of the invention provide the first enabling disclosure directed to these C-glycosides.

In one aspect, the invention relates to a method for preparing C.1-(2,4-pentadiene) derivatives of 2-deoxypyranose sugars. This method is applicable to the preparation of such derivatives of daunosamine. It comprises treating the 2-deoxypyranose, which has a leaving group at C.1, with a 1-trimethylsilyl-2,4-pentadiene in the presence of a Lewis acid. In another aspect, the invention relates to a method for the preparation of C.1 acetaldehyde derivatives of 2-deoxypyranoses, in particular, of daunosamine, using an analogous process to obtain the C.1 allyl derivatives, and then subjecting these to ozonolysis.

In other aspects, the invention relates to the intermediates so prepared and to the target compounds to which these intermediates are converted. Thus, the invention relates to compounds of the formula:

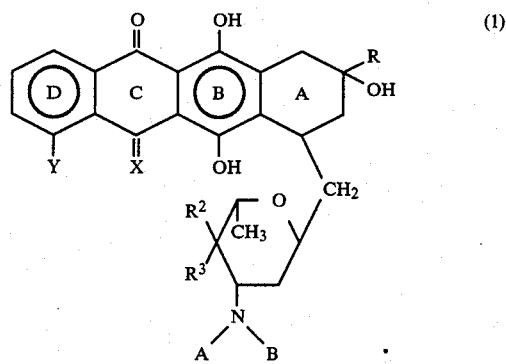

wherein
X is O or NH;
Y is H or OMe; with the proviso that if X=NH, Y must be OMe;
R is COCH$_3$, COCH$_2$OH, CHOHCH$_3$, CHOHCH$_2$OH, H, 1-3C alkyl, 1-2C terminal hydroxyalkyl or the 2-7C alkyl or aryl organic acid esters or 1-6C alkyl ethers thereof; or 13-ketimine (such as hydrazones and oximes) derivatives of COCH$_3$ or COCH$_2$OH;
at least one of R$^2$ and R$^3$ is H, and the other is OH or OCH$_3$; and
A and B are each independently H or alkyl (1-6C), or A and B taken together are morpholino, thiomorpholino, or piperidinyl, optionally mono or di substituted by CN.

The compounds of formula (1) are useful as anti-tumor agents.

Another aspect of the invention relates to compounds of the formula:

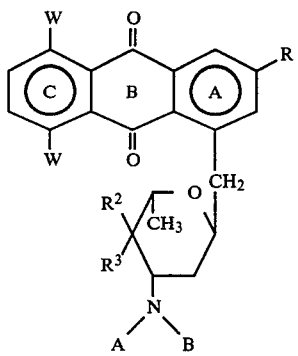
(2)

wherein R, R², R³A and B are as above-defined, and W is H or OH. These compounds of formula (2) are also useful anti-tumor agents.

Other aspects of the invention relate to intermediates in the reactions converting the new products of the novel chemical synthesis methods of the invention to the compounds of formulas (1) and (2).

Thus, in still another aspect, the invention relates to compounds of the formula:

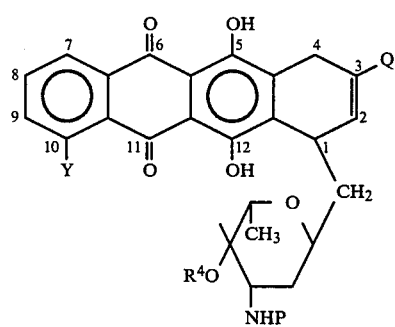
(3)

wherein
 Y is as above-defined;
 P is a protecting group, such as acetyl, trichloroacetyl, or, optimally trifluoroacetyl;
 R₄ is H or a protecting group, such as acyl (1–4C), or optionally substituted aroyl (6–15C); and
 Q is H, alkyl (1–3C), OMe, OEt, —OCH₂CH₂OMe, —O-tetrahydropyranyl, Br, or COOMe.

The compounds of formula (3) result from modifying a polycyclic ring system which results from the Diels-Alder condensation of the appropriate pentadienyl glycosides with the appropriate anthracene tetrone analogs. This polycyclic ring system is contained in the compounds of formula (4):

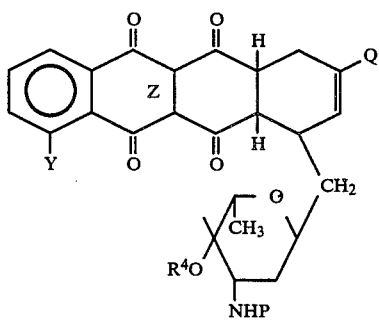
(4)

In still another aspect, the invention relates to the compounds of formula (4) wherein Q, P, Y and R⁴ are as above-defined; and
 wherein the dotted line at Z indicates either a π bond or an epoxide ring.

In still another aspect, the invention relates to compounds of formula (5) which are intermediates analogous to those of formula (4) but which result from Diels-Alder condensation with a naphthalene analog. The compound of formula (5) have the structure:

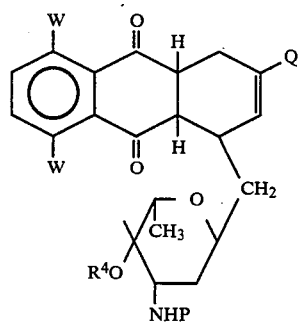
(5)

wherein P, Q, R⁴ and W are as above-defined.

In still other aspects, the invention relates to compounds of the formulas:

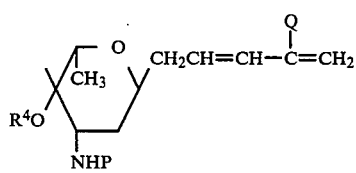
(6)

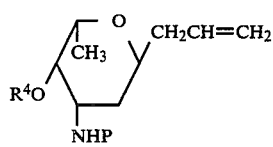
(7)

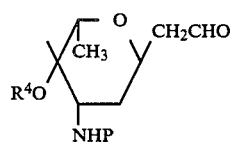
(8)

wherein P, Q and R⁴ are as set forth above. Compounds of the formula (6) where Q is H, CH₃, OMe, OEt, —OCH₂CH₂OMe, or —O-tetrahydropyranyl, and the compound of formula (7) are obtainable as the direct substitution products in the pentadienylation or allylation method of the invention. Compound (8) is the ozonolysis product of compound (7). Compounds of formula (6) wherein Q is as above, and also wherein Q is ethyl, propyl, isopropyl, Br, or COOMe, are obtainable by a Wittig reaction using the compound of formula (8).

MODES OF CARRYING OUT THE INVENTION

A. Definitions and General Parameters

As used herein, "alkyl" is defined as a straight or branched chain hydrocarbon substituent having the designated number of carbon atoms; alkoxy is —OR wherein R is alkyl as above-defined; acyl is

wherein R is alkyl as above defined.

"Aryl" refers to a substituent containing a benzene ring which is linked to the substituted compound referred to either directly, or through a lower alkyl (1–4C) chain. Aryl substituents are, therefore, exemplified by phenyl, phenylethyl, 2-phenyl-2-methylpropyl, and the like. Aroyl is

wherein Ar is aryl as above defined.

The alkyl or aryl substituents (including those which constitute the alkyl portion of alkoxy or acyl or the aryl portion of aroyl) referred to herein may, if so designated, optionally be substituted by one to three substituents selected from the group consisting of hydroxy, alkoxy (1–4C), carbonyl (C=O), carbalkoxy (COOR, wherein R is alkyl) or CN. Substitutions may also include multiple substition by halo such as fluoro, chloro, bromo, or iodo. In the case of aryl substituents these optional substituents may also include alkyl (1–4C) and nitro.

A 2-deoxy hexopyranose (or other substrate) which is "activated", for example, in the 1-position is "activated" by the presence of a good leaving group in that position. The daunosamine sugars may conveniently be activated in the 1-position by esterifying the —OH with an aroyl group, especially p-nitrobenzoyl.

It will be noted that the compounds claimed herein contain a number of chiral centers. Where the depiction of such chiral centers is ambiguous, it is understood that either configuration comes within the denoted species of the formula. The ordinary conventions of projection formulas are used where configuration is specified. If it is desired to separate the compounds into forms which are represented by only one configuration, this is possible using standard techniques for the separation of organic chemicals, such as recrystallization, chromatography, thin layer chromatography, and the like. All of the compounds of the invention contain daunosamine or a protected form, stereoisomer, or derivative of daunosamine. Thus compounds of the invention contain configurations at the daunosamine chiral centers which are already fixed, and all of the permutations of the remaining chiral centers will generate compounds which are diastereomers with respect to each other, permitting standard separation techniques to be used.

It should be noted that in the compounds of formula (1), which represent end-products of pharmaceutical applicability, the hydroxyl and methylene bridge on ring A occupy chiral carbons. The compounds of the invention include all of the stereoisomers, although those which are isosteres of the adriamycin series are preferred. Those compounds which are direct products of Diels-Alder addition (formulas (4) and (5)) under most conditions contain the methylene link from ring A to daunosamine and the two cis hydrogens at the A/B ring fusion on opposite sides of the ring.

When performed under optimum conditions the substitution which leads to the formation of the pentadienyl glycosides or allyl glycosides is stereoselective in accord with results predicted by the anomeric effect, enhanced in some cases by participation of an O-acyl or O-aroyl group at C-4. To the extent that stereoselectivity is not realized, the desired stereoisomer may be separated using standard separation techniques.

B. General Reactions and Modes of Preparation

B.1. Summary

At the heat of the invention is an effective, and, optimally, stereoselective method for forming the C.1 glycosides of 2-deoxy-hexopyranoses. The method comprises treating the substrate 2-deoxy-hexopyranose with 1-trimethylsilyl-2,4-pentadiene or 1-trimethylsilyl-2-propene to obtain the corresponding C.1-(2,4-pentadienyl) or C.1 allyl glycoside respectively. Either of these glycosides may be converted to the corresponding pyranosyl acetaldehyde by ozonolysis.

The products of the reactions which represent the methods of the invention are particularly important when the pyranose substrate is daunosamine (i.e., 2,3,6-trideoxy-3-amino-L-lyxohexopyranose). The pentadienyl products are capable of reacting with suitable dieneophiles included in polycyclic naphthalene or anthracene based systems to obtain C glycosides of anthracene or naphthacene polycyclic systems, respectively. These products are readily convertible to adriamycin or ametantrone/mitoxantrone analogs with anti-tumor activity.

The allyl glycoside products are primarily useful by virtue of their ability to be converted to the corresponding acetaldehyde derivatives which can then be used as substrates for Wittig type reactions to obtain pentadienyl glycosides that bear a greater variety of Q substituents than are obtainable directly using a trimethylsilyl pentadiene.

In short, the methods of the invention offer both a general method for forming C.1 allyl or pentadienyl substituted 2-deoxy-hexopyranoses, and a method specifically for obtaining intermediates in the synthesis of compounds with anti-tumor activity. The routes made possible to obtain these compounds are set forth in schematic form in reaction scheme 1.

Reaction Scheme 1

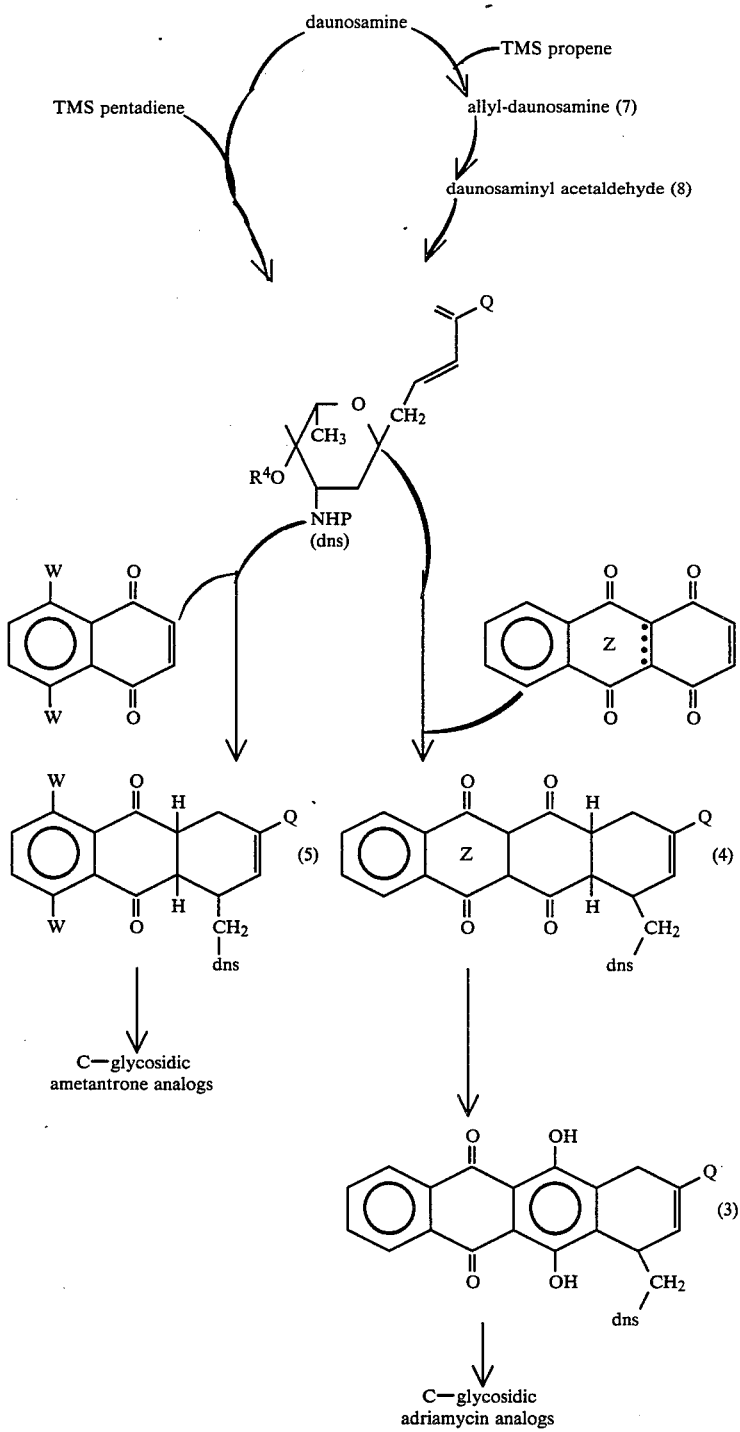

If the pentadienyl daunosamine is obtained directly (left route), Q must be H, methyl, OMe, OEt, —OCH$_2$CH$_2$OMe, or —O-tetrahydropyranyl and the product compound of formula (1) or (2) will be limited accordingly. R in the compounds of formula (1) or (2) thus produced must be H or methyl, or embodiments of R obtainable by addition to an A-ring carbonyl, as further described below. Additional embodiments of R may be obtained, however, by use of the Wittig reaction with the daunosaminyl acetaldehyde of formula (8) (right hand route).

The resulting C-glycosidic analogs of the adriamycin group are then used in a manner similar to that disclosed with respect to the adriamycin group per se, as, for example, set forth in U.S. Pat. No. 4,464,529 issued 7 Aug. 1984 to the same assignee, and incorporated herein by reference. The C-glycosidic ametantrones/mitoxantrones are used as described by Wallace, R. E., et al, Cancer Res (1979) 39:1570; (1980) 40:1427 incorporated herein by reference.

B.2. Allylation Pentadienylation Reactions

In the most general terms, a 2-deoxyhexapyranose sugar substrate "activated"—i.e., containing a suitable leaving group, at position 1 is treated with either allyl trimethylsilane, 2,4-pentadienyl trimethylsilane or the corresponding 2-methoxy-, 2-ethoxy-, 2-methyl-, 2-(2-methoxy)ethoxy- or 2-tetrahydropyranoxy- derivatives of 2,4-pentadienyl trimethylsilane in the presence of a Lewis acid. The trimethylsilane starting materials are available by synthesis using known methods. Any available allyl or pentadientyl trimethylsilane compound can be used and the foregoing are listed as among those previously synthesized.

The substrate sugar is a 2-deoxyhexapyranose having a suitable leaving group at position 1. Such leaving groups include aroyl substitutents such as benzoyl, toluoyl, or p-nitrobenzoyl or may be fluoro. However, the p-nitrobenzoyl leaving group is extremely successful, and the reaction is optimally stereoselective when this leaving group is used. Alternative leaving groups may result in loss of stereoselectivity. Accordingly, the p-nitrobenzoyl leaving group is highly preferred and it is, indeed, pointless to utilize others as the p-nitrobenzoyl derivative is quite easily made, and is entirely satisfactory. The $\alpha$ p-nitrobenzoyl (pNB) derivative of daunosamine, for example, yields almost exclusively the $\alpha$ glycosylated product. The remaining substituents on the pyranose ring may influence the stereoselectivity; in particular an acyl or aroyl group in the 4 position of daunosamine aids in the formation of the $\alpha$ derivative.

The substrate sugar may be any 2-deoxyhexopyranose and may have additional deoxy positions, as well as amino substitutions. That is, positions 3, 4, and 6 may each be, independently, OH as in the basic pyranose structure, deoxy, or deoxyamino, wherein the hydroxy and amino groups may occupy either of the two possible chiral configurations.

If amino groups are present, they must be protected by suitable protecting groups such as acyl or aroyl. A particularly useful protecting group is trifluoroacetyl. This group is entirely successful, easily attached, easily removed when desired, and quite effective. While alternate protecting groups could, in principle, be used, as was the case with the pNB derivative of the C.1 hydroxyl, there is no particular point in seeking alternatives in the face of this success.

Hydroxyl groups are desirably, but not necessarily protected as well. Suitable protecting groups include benzoyl, pNB, and other acyl or aroyl esters. pNB appears particularly satisfactory for this purpose.

A particularly preferred substrate, because of the utility of the products, is a protected daunosamine, e.g., 1,4-di-O-p-nitrobenzoyl-2,3,6-trideoxy-3-trifluoroacetamido-$\alpha$-L-lyxo-hexopyranose.

The reaction is conducted in the presence of a Lewis acid such as $TiCl_4$ or $Me_3SiOSO_2CF_3$, and most preferably in the presence of boron trifluoride etherate. The reaction is carried out by preparing a mixture of the pyranose and silane reagents in the presence of a moderately polar aprotic organic solvent such as, for example, acetonitrile, ether, or tetrahydrofuran, preferably acetonitrile. The Lewis acid, for example, boron trifluoride in ether solution is added slowly to the mixture, preferably dropwise. The reaction is allowed to increase in temperature to approximately room temperature and stirred for sufficient time to allow the reaction to go substantially to completion, usually around 2–4 hr. The product is isolated from the reaction mixture using ordinary means, such as extraction into an inert organic solvent from aqueous base, followed by evaporation of solvent, and subjected to subsequent standard purification techniques.

The reaction conditions are quite mild and straightforward, and depending on the stereochemistry of the ring, and the nature of the leaving group, a high yield of the desired $\alpha$ product (i.e., the $\alpha$ glycoside) is obtained.

B.3. Alternative Method to Form the C.1 Pentadienyl Glycosides

An alternate approach to prepare the C.1 pentadienyl daunosamines of formula (6) takes advantage of the formation of the corresponding allyl glycoside, prepared as in paragraph B.2. The allyl compound is converted by standard ozonolysis procedures to the 2-daunosaminoyl acetaldehyde derivative, as in reaction scheme 2, which is then converted to the corresponding pentadienyl derivative by a standard Wittig reaction using a compound of the formula

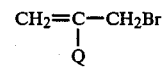

wherein Q is as above-defined.

Reaction Scheme 2

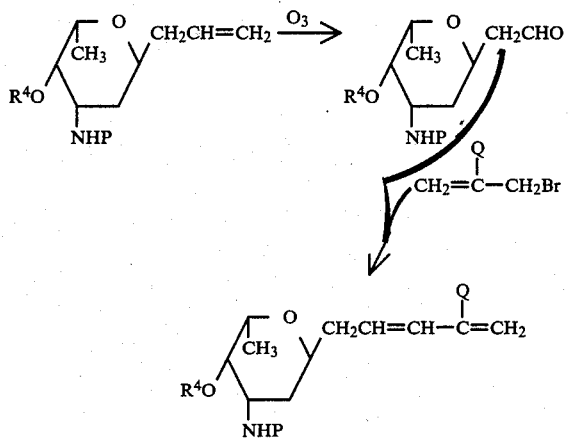

The resulting pentadienyl glycosides may be used in the Diels-Alder reaction of paragraph B.4.

B.4. Diels-Alder Reactions

When daunosamine or its derivatives are used as substrates for the pentadienylation reactions of the invention as described in paragraph B.2 or in the conversion sequence of paragraph B.3, the resulting C.1-(2,4-pentadienyl)glycosides can be converted, by Diels-Alder reaction with suitable polycyclic systems, to intermediates in the formation of adriamycin analogs or the corresponding ametantrones.

The carbohydrate substrate for the Diels-Alder reaction is an N-protected 2,3,6-trideoxy-3-amino-$\alpha$-L-lyxohexopyranoside having the C.1 pentadienyl substitution. The amino group may be protected by any suitable acylating agent such as and preferably, for example, trifluoroacetyl. This amino group may then, subsequently, be converted to alternative N-derivatives as will be described below.

In the Diels-Alder, and subsequent reactions the 4-hydroxy group of the daunosamine may be in the free hydroxyl form, or may be esterified by reaction with suitable carboxylic acid derivatives to give the acyl or aroyl or substituted aroyl ester. The ester group may later be removed by standard hydrolysis procedures.

The dienophile used for the Diels-Alder reaction in preparing the useful intermediates to the adriamycin or ametantrone analogs is generally a polycyclic dione or tetrone, and the product is a naphthacene or anthracene derivative. For the anthracene (ametantrone analog) products, a useful dieneophile is 5,8-dihydroxy-1,4-naphthaquinone. For adriamycin analogs, useful dieneophile substrates are compounds of the formula:

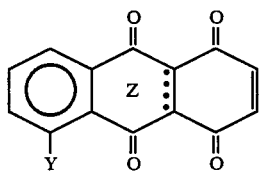

wherein Y and Z are as above-defined.

The Diels-Alder reaction shown in scheme 3 is performed in the presence of an inert aprotic solvent such as, for example, toluene. The reaction is carried out under an inert atmosphere such as nitrogen, at a temperature range of about 60° C.-100° C., preferably about 80° C.-85° C. for approximately several hours. The product is isolated using routine procedures.

the opposite side of the ring from the hydrogens of the A/B ring bridge (this resulting from the endo reaction); thus the representations in Reaction Scheme 3 are of diastereomeric pairs which may be separated using standard chromatographic techniques.

B.5. Conversion to Target Compounds

For the ametantrone analogs, the Diels-Alder products are directly convertible to the target compounds of formula (2) by modifying the A ring substituent Q to obtain the desired R, if necessary, followed by aromatization of the A ring. For the adriamycin analogs, preliminary modification of the B and C rings may be required prior to adding the elements of water to the A rings double bond.

B.5.a. Adriamycin Analogs

The Diels-Alder products of paragraph B.4 which will lead to the target compounds of the formula (1) may be separated into desired stereoisomers at any convenient stage of the following reactions.

The first steps of the conversion to the target compounds result in enolization of the carbonyl moieties of ring B to a hydroquinone. This is a one-step reaction if Z is a $\pi$ bond, but a three-step reaction if Z represents an epoxide. Where Z represents an epoxide, the compound of formula (4) is first reduced to the corresponding alkene in a two step reaction using, first sodium dithionite to aromatize the C ring, followed by treating with lead tetraacetate to give the desired alkene. This alkene is, of course, the direct product of the Diels-Alder reaction when Z is a $\pi$ bond. The alkene is then treated with acid in the presence of a polar solvent and Reaction Scheme 3

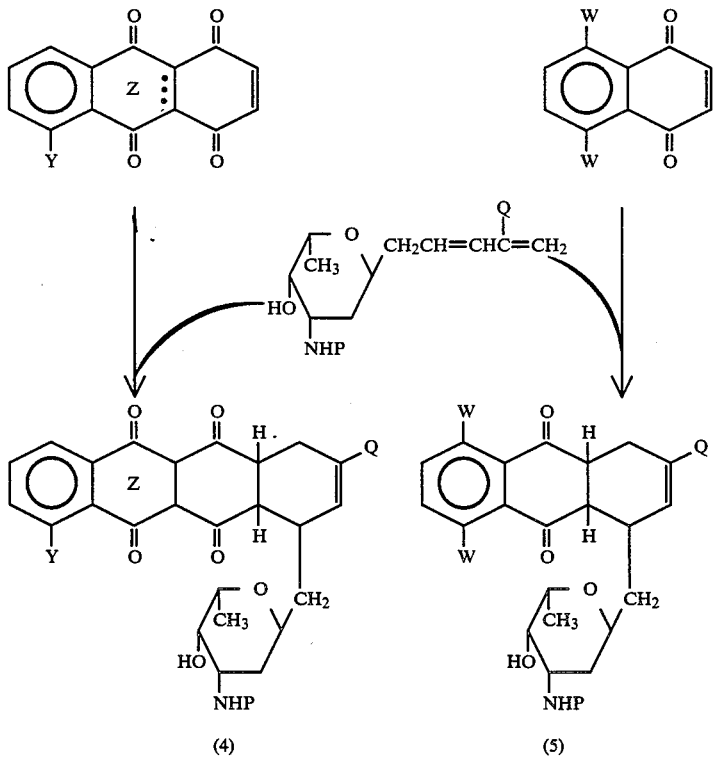

The 4-hydroxyl is shown as unprotected; however in a preferred embodiment a pNB group would be used for this purpose. The linking methylene in the product is on in an inert atmosphere at approximately room temperature for sufficient time to permit the desired enolization to take place. This time is usually 2–6 hr, roughly around 4 hr.

The desired product of formula (3) is accompanied by a side product of formula (11) as shown in reaction scheme 4. The compound of formula (11) may also have useful anti-tumor activity when modified by removal of protecting groups as described in paragraph B.6 below.

formula (11) results in analogous compounds with antitumor activity.

The addition to the A ring $\pi$ bond will be conducted in a manner dependent on the nature of Q. If Q is H in formula (3) this will be done with a regioselective agent such as a bulky alkyl borane, preferably 9-BBN under conditions suitable for this reagent (see, for example, Brown, H. C., et al, J Am Chem Soc (1977) 99:3427). The addition results in a compound which differs from

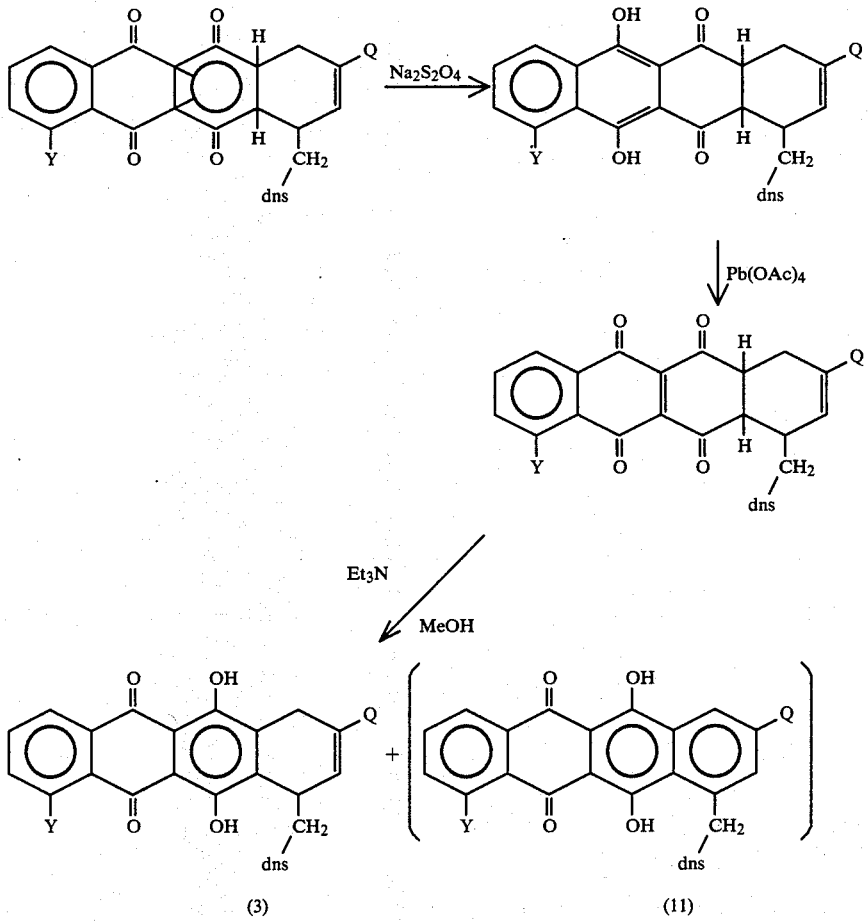

The protecting group for the amino, which is, ideally, trifluoroacetyl is still present. The hydroxyl at position 4 will, under most conditions also retain the protecting group which was present through the previous reactions, although the 4-position is shown here with a free OH.

The remaining steps to obtain the desired target compounds depend on the nature of Q and the nature of R. Where Q is identical to the desired R in the target compound, the conversion is simplified accordingly. (It should be apparent that Q and R are only identical if Q is H or alkyl (1–3C).) The compounds of formula (3) then need only to be further modified by addition of the elements of water to the ring A double bond, and by removal of the TFA protecting group to obtain the embodiments of the compounds of formula (1) wherein $R^2$ is H, $R^3$ is OH, and A and B are both hydrogen. Further modification of $R^2$, $R^3$, A and B may also be effected as described in paragraph B.6. Similarly, removal of protecting groups from the side products of a compound of formula (1) wherein R is H only in requiring the removal of protecting groups, and optional modification of the sugar substituents, as described in paragraph B.6.

For those embodiments of formula (3) wherein Q is alkyl (1–3C), hydration of the double bond will be carried out using customary reagents for the addition of the elements of water.

(If Q is COOMe, the same procedure is followed as for Q=alkyl, but the resultant product of the hydration must then be reduced with, for example, a metal hydride to obtain the corresponding alcohol-i.e., R=CH$_2$OH, which could optionally be esterified or converted to the ether. Compounds of formula (1) which result include, for example, 3-hydroxymethyl-1,2,3,4-tetrahydro-5,12-dihydroxy-1-[(2,3,6-trideoxy-3-amino-α-L-lyxo-hexopyranosyl)-methyl]naphthacene-6,11-dione, 3-butanoylmethyl-1,2,3,4-tetrahydro-5,12-dihydroxy-1-[(2,3,6-trideoxy-3-amino-α-L-lyxo-hexopyranosyl)-methyl]naphthacene-6,11-dione, and
3-butoxymethyl-1,2,3,4-tetrahydro-5,12-dihydroxy-1-[(2,3,6-trideoxy-3-amino-α-L-lyxo-hexopyranosyl)-methyl]naphthacene-6,11-dione.)

For the remaining cases wherein R is not identical with Q, the appropriate hydration product is used to obtain an intermediate with a carbonyl group in the A ring. If Q is H, the hydration product is oxidized using a relatively mild oxidizing agent, such as dimethyl sulfoxide/dicyclohexylcarbodiimide or pyridinium chlorochromate under neutral conditions to obtain the corresponding ketone. If Q is a leaving group such as Br or OMe, no oxidation is necessary. An acetylide is then added to the ketone as shown in reaction scheme 5, and the product converted to the desired embodiments of R.

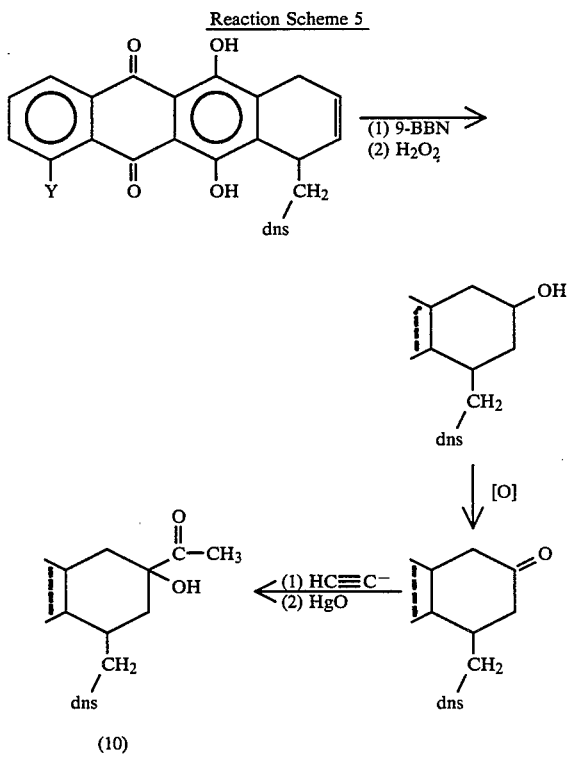

The ketone is treated with a sodium or lithium acetylide, or the corresponding magnesium bromide acetylide and hydrated in the presence of mercuric oxide to obtain the addition product shown in reaction scheme 5 as formula (10). Modifications of the acyl group to obtain the various alternate embodiments of R in formula (1) employ conversions known in the art.

The compound of formula (10) may, itself, be deprotected and modified as desired according to the procedures set forth in paragraph B.6 to obtain embodiments of the formula (1) wherein R is COCH$_3$, such as, for example, 3-acetyl-1,2,3,4-tetrahydro-5,12-dihydroxy-1-[(2,3,6-trideoxy-3-amino-α-L-lyxo-hexopyranosyl)methyl]naphthacene-6,11-dione.

The acyl may also be reduced to the corresponding alcohol, thus providing an intermediate for conversion by deprotection and modification procedures to compounds of formula (1) wherein R is CHOHCH$_3$, such as 3-(1-hydroxyethyl)-1,2,3,4-tetrahydro-5,12-dihydroxy-1-[(2,3,6-trideoxy-3-amino-α-L-lyxohexopyranosyl)methyl]naphthacene-6,11-dione. This may optionally be followed by derivatization to the ester or ether.

Reaction with bromine at the α carbon of the acyl substituent permits formation of embodiments wherein R contains a terminal hydroxy or ester or ether derivative thereof. By treating the compound of formula (10) with bromine, followed by substitution of the bromo substituent in base, compounds of the formula (1) are obtained wherein R is COCH$_2$OH, such as 3-(2-hydroxyacetyl)-1,2,3,4-tetrahydro-5,12-dihydroxy-1-[(2,3,6-trideoxy-3-amino-α-L-lyxo-hexopyranosyl)methyl]-naphthacene-6,11-dione.

The intermediates bearing the —COCH$_2$OH substituent may be used to obtain various additional embodiments of R. In one conversion, the carbonyl is reduced to the alcohol, by treating with an appropriate metal hydride, to obtain compounds suitable for deprotection and modification to the various compounds of formula (1) wherein R is CHOHCH$_2$OH, such as 3-(1,2-dihydroxyethyl)-1,2,3,4-tetrahydro-5,12-dihydroxy-1-[(2,3,6-trideoxy-3-amino-α-L-lyxo-hexopyranosyl)methyl]naphthacene-6,11-dione. Alternatively, the carbonyl may be reduced to the methylene, leaving intact the terminal hydroxy, thus permitting conversion to compounds of formula (1) wherein R is CH$_2$CH$_2$OH, and their corresponding esters and ethers. Exemplary of such compounds is 3-(2-hydroxyethyl)-1,2,3,4-tetrahydro-5,12-dihydroxy-1-[(2,3,6-trideoxy-3-amino-α-L-lyxohexopyranosyl)methyl]naphthacene-6,11-dione.

Intermediates, or compounds of the formula (1) wherein R is COCH$_3$ or COCH$_2$OH may also be converted to the corresponding ketimine derivatives by reaction with the appropriate amine, hydroxylamine or hydrazine. Thus, these compounds may be formed by reaction with compounds of the formula KNH$_2$ wherein K is OH or NHS, wherein S is an alkyl or aryl substituent.

The foregoing conversions are summarized in reaction scheme 6.

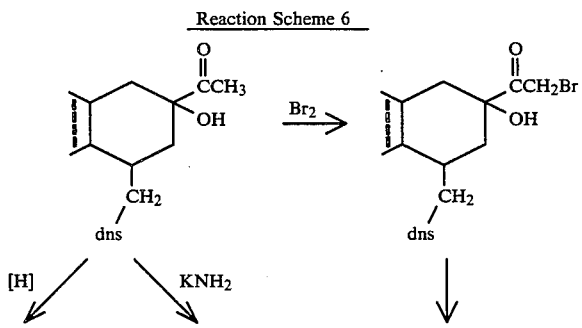

Reaction Scheme 6
-continued

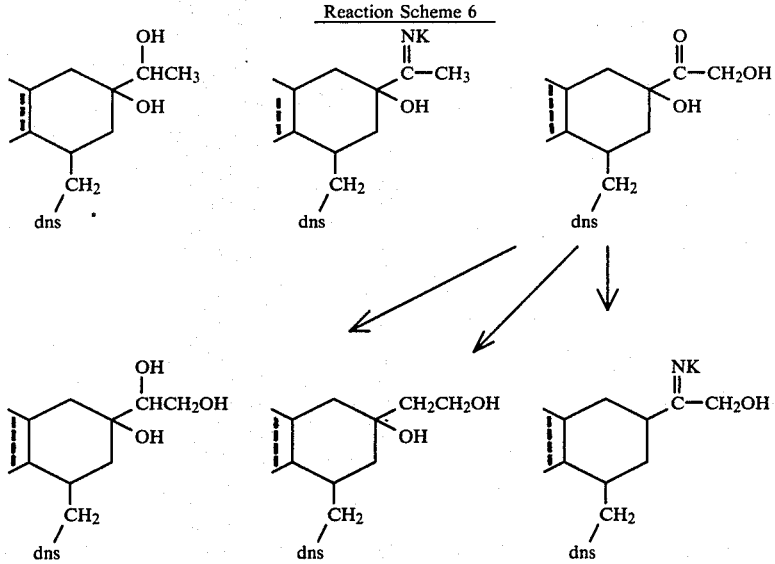

B.5.b. Ametantrone Analogs

The compounds of the invention of formula (2) which are ametantrone analogs may be prepared from the intermediate obtained by Diels-Alder reaction without preliminary modification of the polycyclic system. The final step will be aromatization of the A ring as shown in reaction scheme 7.

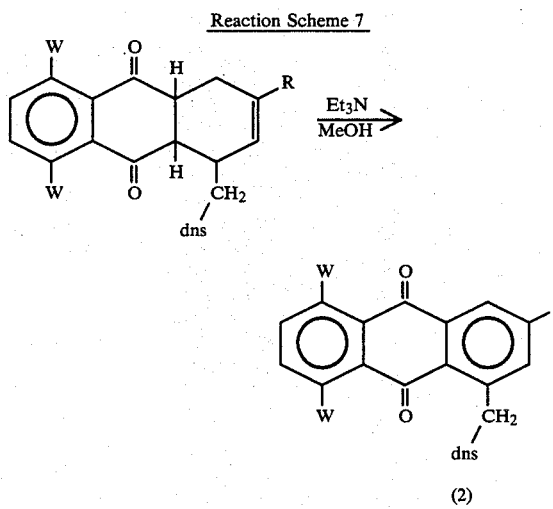

If Q is identical to R, which is possible if Q is H or alkyl (1–3C), or convertible to R, which is the case if Q is COOMe, this is the only step (other than deprotection and sugar group modification) required. If, however, Q is not the same as or convertible to Q, the reaction shown in scheme 7 must be preceded by a series of reactions to obtain the desired embodiment.

This is done by preparing the compound of formula (5) wherein Q is H or a leaving group, and conducting procedures precisely analogous to those set forth in paragraph B.5.a, i.e. addition of the elements of water to the π bond, oxidation, if necessary, to the ketone, addition of acetylide to the ketone, and modification of the resulting acetyl substituent. The coversions are precisely those shown for the adriamycin analogs in reaction scheme 6. Aromatization of the A ring (which does not, in this case, contain a π bond) is the final step in modification of the polycyclic system and is conducted by a modification of the conditions shown in reaction scheme 7.

B.6. Protective Group Removal and Sugar Modification

For compounds of either formula (1) or (2), the protecting TFA group from the 3-amino position is removed, and, if desired, replaced by suitable substituents to obtain the embodiments of formula (1) or (2) wherein A and B are as defined. These conversions have been set forth in some detail in U.S. Pat. Nos. 4,035,566; 4,301,277; and 4,464,529; as well as U.S. Ser. No. 598,016, filed Apr. 14, 1984, and assigned to the same assignee, all incorporated herein by reference. Modification of the ring system so as to obtain X=NH is possible in those embodiments wherein Y is OMe, as described in U.S. Pat. No. 4,109,076 incorporated herein by reference. Similarly, the hydroxyl group at position 4 may be methylated, or may be reduced to form the 4-deoxy sugar by means known in the art.

EXAMPLES

The following examples are intended to illustrate but not to limit the invention.

EXAMPLE 1

Preparation of 1-(2,3,6-Trideoxy-4-O-p-nitrobenzoyl-3-trifluoroacetamido-α-L-lyxo-hexopyranosyl)-2-propene The procedure was similar to that disclosed by Kozikowski, et al, Tetrahedron Lett (1983) 24:1563.

541 mg (1.00 mmoles) of 1,4-di-O-p-nitrobenzoyl-2,3,6-trideoxy-3-trifluoroacetamido-α-L-lyxohexopyranose;

505 mg (4.00 mmoles) of allytrimethylsilane; and 157 mg (1.10 mmoles) of boron trifluoride etherate were used.

The boron trifluoride was added dropwise to a cold mixture of pyranose and silane in 20 ml of acetonitrile, protected from moisture in an ice bath. The reaction mixture allowed to reach room temperature, and stirred at room temperature for 3 hr. The reaction was diluted with 50 ml of saturated sodium bicarbonate and extracted with 3×30 ml of ethyl ether. The ether was dried over MgSO$_4$, filtered and evaporated to dryness. The oily residue, 420 mg (101%), was chromatographed on silica gel 2×[20 cm×20 cm×2 mm] with 25% EtOAc/hexane and gave R$_f$=0.4. Elution yielded 350 mg (94%) of foam. This residue was crystallized from 25 ml Et$_2$O/hexane (1/6) to give 350 mg (84%) 1-(2,3,6-trideoxy-4-O-p-nitrobenzoyl-3-trifluoroacetamido-α-L-lyxo-hexopyranosyl)-2-propene;; mp 138°–139° C. HPLC silica gel chromatography using 1% isopropanol/hexane gave 100% one isomer. Analysis was consistent with C$_{18}$H$_{19}$F$_3$N$_2$O$_6$ and NMR was consistent with the expected allyl pyranose.

EXAMPLE 2

Preparation of (2,3,6-Trideoxy-4-O-p-nitrobenzoyl-3-trifluoroacetamido-α-L-lyxo-hexopyranosyl)acetaldehyde 208 mg (0.500 mmoles) of the pyranosyl propene from Example 1 was dissolved in 25 ml McCl$_2$ and chilled to −78° C. (dry ice acetone bath). O$_3$ was bubbled through (from a O$_3$ generator) until a permanent blue color appeared. The blue solution was stirred at −78° C. for 4 hr. The excess O$_3$ was removed by bubbling argon into the reaction mixture, and 1 ml of dimethyl sulfide added at −78° C. to destroy the ozonide intermediate. The reaction was allowed to reach room temperature; TLC showed the presence of intermediate (two spots) but no aldehyde. MeOH (1 ml) was added and the aldehyde slowly began to form, as followed by TLC. After 3 days stirring, and addition of 5 ml MeOH, most intermediate was converted to aldehyde. The solution was evaporated to dryness to yield 190 mg (91%) of (2,3,6-trideoxy-4-O-p-nitrobenzoyl-3-trifluoroacetamido-α-L-lyxo-hexopyranosyl)acetaldehyde. The residue was chromatographed on 20×20 cm×2 mm thick silica gel plate and developed with 50% EtOAc/hexane. The product was eluted with ethylacetate to give 158 mg of aldehyde. The identity of product with the expected aldehyde was confirmed by mass spectroscopy (m/e=418) and by NMR.

EXAMPLE 3

Preparation of (E)-1-(2,3,6-Trideoxy-4-O-p-nitrobenzoyl-3-trifluoroacetamido-α-L-lyxo-hexopyranosyl)-2,4-pentadiene The procedure was similar to that of Kozikowski, et al (supra).

2.80 g (5.17 mmoles) of 1,4-di-O-p-nitrobenzoyl-2,3,6-trideoxy-3-trifluoroacetamido-α(β)-L-lyxo-hexopyranose (α/β ratio of ¼);

3.15 g (20.7 mmoles) of (E)-(2,4-pentadienyl)-trimethylsilane; and 0.970 g (6.21 mmoles) of boron trifluoride; etherate were used.

The boron trifluoride was added dropwise to a mixture of the pyranose and silane in 100 ml of acetonitrile, protected from moisture in an ice bath. The reaction was allowed to reach room temperature, and then stirred at room temperature for 3 hr. The reaction mixture was diluted with 250 ml of saturated sodium bicarbonate and extreacted with 3×100 ml of ethyl ether. The ether was dried over MgSO$_4$, filtered, and evaporated to dryness to yield 2.6 g of (E)-1-(2,3,6-trideoxy-4-O-p-nitrobenzoyl-3-trifluoroacetamido-α-L-lyxo-hexopyranosyl)-2,4-pentadiene (114%) as an oil. The residue was placed on a silica gel column and developed with 10% ethyl acetate/hexane to obtain 1.82 g (85%) of pure product. A small sample of the material from the silica gel was purified on thick layer silica gel with 25% EtOAc/hexane. The R$_f$ was 0.4, and the spot, which was eluted with CHCl$_3$, showed 100% purity on HPLC. Elemental analysis of this sample was consistent with C$_{20}$H$_{21}$F$_3$N$_2$O$_6$ and NMR (400 MHz).

EXAMPLE 4

Preparation of (E)-1-(2,3,6-Trideoxy-3-trifluoroacetamido-α-L-lyxo-hexopyranosyl)-2,4-pentadiene (Removal of p-nitrobenzoyl from position 4)

0.700 g (1.58 mmoles) of the pentadienyl pyranose prepared in Example 3 was mixed with 10 ml of diisopropyl amine and 50 ml of methanol and stirred at room temperature for 18 hr. The solution was evaporated to dryness. The residue was placed on two 20×20 cm×2 mm silica gel thick plates and developed with (1/1) hexane/ethylacetate. R$_f$=0.33. The eluate (ethyl acetate) contained 380 mg (82%) of foam, which was crystallized from 30 ml of hexane to give 359 mg (77%) of (E)-1-(2,3,6-trideoxy-3-trifluoroacetamido-α-L-lyxo-hexopyranosyl)-2,4-pentadiene, mp 111°–112° C. Analysis was consistent with C$_{13}$H$_{18}$F$_3$NO$_3$ and the NMR (300 MHz) matched that expected for the desired product.

EXAMPLE 5

(The Diels-Alder Reaction Step) Preparation of 5a,11a-Epoxy, 1,4,4a,5a,11a,12a-hexahydro-1-[(2,3,6-trideoxy-4-benzoyl-3-trifluoroacetamido-α-L-lyxo-hexopyranosyl)-methyl]-naphthacene-5,6,11,12-tetrone A. The procedure was similar to that of Chandler, et al, *J Chem Soc Perkin I* (1980) 1007. The pentadienyl pyranose from Example 4 was first benzoylated at the 4 position. Benzoyl chloride was added to a solution of 150 mg (0.511 mmoles) pyranose in 25 ml of dry pyridine, with magnetic stirring, in an ice bath and protected from moisture. The mixture was brought to room temperature, heated to 45° C. for 4 hr and then stirred at room temperature for 18 hr. The solution was poured into 100 ml ice water and extracted with 2×50 ml CHCl$_3$. The CHCl$_3$ was washed with 50 ml 1N HCl, 50 ml saturated NaHCO$_3$ and 50 ml H$_2$O. The CHCl$_3$ was then dried over MgSO$_4$, filtered and evaporated to dryness to yield 210 mg (103%) of a syrup. This residue was chromatographed on a 20×20 cm×2 mm thick silica gel plate with 25% EtOAc/hexane and gave R$_f$∼0.45. The eluted (EtOAc) product was 182 mg which remained a gum on "recrystallization" with Et$_2$O/hexane or MeOH/H$_2$O. The IR showed no OH and good benzoyl carbonyl peaks and the NMR was consistent with the expected product.

A mixture of 170 mg (0.427 mmoles) of the above product gum and 120 mg (0.472 mmoles) of 4a,9a-epoxy-4a,9a-dihydro-anthracene-1,4,9,10-tetrone in 10 ml of toluene was heated at 90°–95° C. for 4 hr under N$_2$. The reaction mixture was cooled, 10 ml of hexane added, and the mixture chilled and filtered to give 235 mg of brown solid. The mass spectrum showed m/e, 651 and NMR (90 MHz) shows two $C_6$'s at 1.15 (d) and 1.16 (d), $J_{5,6}=6$ Hz, indicating the presence of the two expected diastereomers of 5a,11a-epoxy-1,4,4a,5a,11a,12a-hexahydro-1-[(2,3,6-trideoxy-4-benzoyl-3-trifluoroacetamido-α-L-lyxo-hexopyranosyl)-methyl]-naphthacene-5,6,11,12-tetrone in equal amounts. The $C_4$ proton peaks at 5.26 and 5.29 were two broad singlets indicating the presence of pyranose sugar.

B. In an analogous manner, but using instead of the 4-O-benzoyl lyxo-hexopyranose derivative, the 4-OH and 4-O-p-nitrobenzoyl derivatives, respectively, there were prepared: the 4-hydroxy analog of the compound of paragraph A: 5a,11a-epoxy-1,4,4a,5a,11a,12a-hexahydro-2-[(2,3,6-trideoxy-3-trifluoroacetamido-α-L-lyxo-hexopyranosyl)-methyl]-naphthacene-5,6,11,12-tetrone; and the 4-O-p-nitrobenzoyl analog of the compound of paragraph A: 5a,11a-epoxy-1,4,4a,5a,11a,12a-hexahydro-2-[(2,3,6-trideoxy-4-O-p-nitrobenzoyl-3-trifluoroacetamido-α-L-lyxo-hexopyranosyl)-methyl]-naphthacene-5,6,11,12-tetrone The 4-hydroxy analog gave two peaks of equal amounts of diastereomers on C-18 HPLC using a 0.1M $NaH_2PO_4/CH_3CN$ gradient. HR-MS showed m/e 547.1452 (calc for $C_{27}H_{24}F_3NO_8=547.1454$); NMR gave $C_6$ protons at 1.22(d) and 1.25(d) $J_{5,6}=6.4$ Hz.

The 4-O-p-nitrobenzoyl analog gave a mp of 160–210 (dec) and m/e=696.

EXAMPLE 6

Conversions of the Polycyclic Systems (Steps in Obtaining Intermediates of Formula (3))

The Diels-Alder product from the condensation of the epoxyanthracene system was converted to a compound of formula (3) in a three step process that includes a two step conversion of the epoxide to the corresponding alkene (paragraphs A and B), followed by aromatization of the B ring.

A. Reduction to the Naphthacene Dione

A.1. A sample of 220 mg (0.338 mmoles) of the product of Example 5, paragraph A in 5 ml of MeOH was reduced to the hydroquinone with 178 mg (1.10 mmoles) of sodium dithionite in 2 ml $H_2O$. The sodium dithionite solution was added dropwise, to the stirred MeOH solution of the tetrone. After 5 hr, one drop of 1N HCl was added (pH of solution 3–4), and the reaction mixture was diluted with 25 ml $H_2O$ and extracted with 25 ml $CHCl_3$. The $CHCl_3$ was washed with saturated $NaHCO_3$ solution. The $CHCl_3$ was then dried over $MgSO_4$, filtered and evaporated to dryness to give 130 mg (61%) of 1,4,4a,12a-tetrahydro-6,11-dihydroxy-1-[(2,3,6-trideoxy-4-O-benzoyl-3-trifluoroacetamido-α-L-lyxo-hexopyranosyl)methyl)]-naphthacene-5,12-dione. The residue was chromatographed on 2×(20×20 cm×2 mm) silica gel plates, developed with 25% EtOAc/hexane and gave a broad band at 0.2 to 0.5 $R_f$ which was eluted with EtOAc. The 74 mg (35%) of the product was eluted and showed an MS peak at 635. The NMR (90 MHz) showed two $C_6$'s at 0.81 (d) and 1.16 (d).

A.2. In an analogous manner, but using the 4-hydroxy analog prepared in Example 5, paragraph B there was prepared 1,4,4a,12a-tetrahydro-6,11-dihydroxy-1-[(2,3,6-trideoxy-3-trifluoroacetamido-α-L-lyxo-hexopyranosyl)methyl]-naphthacene-5,12-dione. This product gave the two expected diastereomers on C-18 HPLC, 0.1M $NaH_2PO_4/CH_3CN$ gradient; HR-MS gave m/e 533.1670 (calc for $C_{27}H_{26}F_3NO_7=533.1661$); NMR (90M Hz) showed two $C_6$ protons; 1.34(d) and 0.86(d); $J_{5,6}=6$ Hz.

B. Conversion to the Alkene

Sixty mg (0.0941 mmoles) of the product from paragraph A.1 of this Example was treated with 55 mg (0.124 mmoles) of lead tetraacetate. The solution (pink) was stirred for 3 hr. The reaction was diluted with 25 ml $CHCl_3$ and washed with 20 ml of saturated $NaHCO_3$ solution. The $CHCl_3$ was dried over $MgSO_4$, filtered and evaporated to dryness to yield 40 mg (67%) red-brown foam, mostly 1,4,4a,12a-tetrahydro-1-[(2,3,6-trideoxy-4-O-benzoyl-3-trifluoroacetamido-α-L-lyxo-hexopyranosyl)methyl]-naphthacene-5,6,11,12-tetrone. NMR (90 MHz) showed no phenolic OH and two $C_6$ protons at 0.95 (d) and 1.18 (d); $J_{5,6}=6.1$ Hz, indicating two compounds. Two $C_4$ protons giving broad singlets at 5.18 and 5.27 indicate the pyranose sugar; the mass spectrum showed a m/e=635.

C. Enolization of the B Ring

Twenty mg (0.198 mmoles) of trimethylamine in 2 ml methanol under $N_2$ was added to 35 mg (0.0551 mmoles) of the product of paragraph B of this Example, in 5 ml MeOH.

The solution was stirred 4 hr at room temperature and then evaporated to dryness. Upon redissolving in 5 ml of MeOH a red solid precipitated to give 5 mg (14%) of a side product having an aromatized A ring, of formula (11) 5,12-dihydroxy-1-[(2,3,6-tredeoxy-4-O-benzoyl-3-trifluoroacetamido-α-L-lyxo-hexopyranosyl)methyl]-naphthacene-6,11-dione (as indicated by m/e=633). This side product can be further treated to remove protecting groups to give target compounds analogous to the adriamycin compounds of the invention, which also have anti-tumor activity.

The filtrate was evaporated, and the residue was subjected to thick layer silica gel chromatography and 5 mg of the desired product of formula (3), 1,4-dihydro-5,12-dihydroxy-2-[(2,3,6-trideoxy-4-O-benzoyl-3-trifluoroacetamido-α-L-lyxo-hexopyranosyl)methyl]-naphthacene-6,11-dione (as indicated by m/e=635) was recovered by elution of the material at $R_f=0.5$.

EXAMPLE 7

Preparation of 1,4-Dihydro-2,12-dihydroxy-1-[(2,3,6-trideoxy-3-trifluoroacetamido-α-L-lyxo-hexo-pyranosyl)methyl]-naphthacene-6,11-dione A. (Alternate Diels-Alder Condensation)

In a manner analogous to that of Example 5, 60 mg (0.204 mmoles) of (E)-1-(2,3,6-trideoxy-3-trifluoroacetamido-α-L-lyxo-hexopyranosyl)-2,4-pentadiene was mixed with 50 mg (0.21 mmole) of anthracene-1,4,9,10-tetrone in 10 ml toluene and the mixture was heated under $N_2$ at 90°–100° C. for 18 hr. Ten ml of hexane was added and the mixture chilled, and the solid was filtered to give 132 mg (122%) of a mixture containing the desired compound, 1,4,4a,12a-tetrahydro-1-[(2,3,6-trideoxy-3-trifluoroacetamide-α-L-lyxo-hexopyranosyl)methyl]-naphthacene-5,6,11,12-tetrone.

NMR showed a mixture of desired product and compound made by internal Diels-Alder reaction with positions 4a and 9a of the tetrone. As the desired product is unstable to silica gel, it was subjected to aromatization as set forth below without further purification.

B. (Enolization of the B Ring)

The procedure was based on *Beilstein's Handbuch der Organischen Chemie*, 4th ed., 6 3rd suppl, p 5608.

0.204 mmoles of 1,4,4a,12a-tetrahydro-1-[(2,3,6-trideoxy-3-trifluoroacetamido-α-L-lyxo-hexopyranosyl)methyl]-naphthacene-5,6,11,12-tetrone (~50% pure) as prepared in paragraph A was dissolved in 10 methanol and 0.2 ml of methanol saturated with HCl added under an argon atmosphere. A red solid formed. After 4 hr, the mixture was filtered, to give 12 mg (11%) of a solid which contained the desired product 1,4-dihydro-5,12-dihydroxy-1-[(2,3,6-trideoxy-3-trifluoroacetamido-α-L-lyxo-hexopyranosyl)methyl]-naphthacene-6,11-dione which showed a 9:1 isomer ratio on HPLC.

To obtain additional product, filtrate was evaporated to dryness and the residue taken up in 10 ml MeOH and again evaporated to dryness to give 100 mg (92%) of a residue which was chromatographed on a thick silica gel plate 20×20 cm×2 mm and developed by 50% EtOAc/hexane. The eluted 16 mg (15%) of red orange foam was subjected to HPLC and showed a mixture of desired products in a 3/5 ratio and a trace of the side product aromatized A ring isomer of formula (11).

NMR on the chromatographed sample gave $C_6$ protons 0.84(d) & 1.11(d); $J_{5,6}=6$ Hz; phenolic OH 13.68 and 13.46.

EXAMPLE 8

Preparation of 1,4,4a,9a-tetrahydro-1-[(2,3,6-trideoxy-4-O-p-nitrobenzoyl-3-trifluoroacetamido-α-L-lyxo-hexo-pyranosyl)methyl]-anthracene-9,10-dione A. Ninety mg (0.203 mmoles) of (E)-1-(2,3,6-trideoxy-4-O-p-nitrobenzoyl-3-trifluoroacetamido-α-L-lyxo-hexopyranosyl)-2,4-pentadiene and 22.0 mg (0.140 mmoles) of 1,4 naphthoquinone were mixed in 10 ml toluene and the mixture was heated under $N_2$ at 80°–88° C. for 4 hr. The reaction was chilled to 0° C. and filtered to give 55 mg (65%) 1,4,4a,9a-tetrahydro-1-[(2,3,6-trideoxy-4-O-p-nitrobenzoyl-3-trifluoroacetamido-α-L-lyxo-hexo-pyranosyl)methyl]-anthracene-9,10-dione in impure form.

NMR gave 2 $C_6$ protons 1.03(d) and 1.17(d); $J_{5,6}=6.0$ Hz in approximately equal amounts, and two $C_4$ protons 5.22 and 5.34 as broad singlets indicating pyranose sugar.

B. In an analogous manner, the free 4-hydroxy pyranose analog of the 4-p-nitrobenzoyl pyranose tetrahydroanthraquinone derivative of paragraph A was prepared using 60 mg (0.204 mmoles) of (E)-1-(2,3,6-trihydroxy-3-trifluoroacetamido-α-L-lyxo-hexopyranosyl)2,4-pentadiene and 33 mg (0.208 mmoles) of 1,4-naphthoquinone as starting materials. Eighty-five mg (92%) of a tan solid containing the two isomers of 1,4,4a,9a-tetrahydro-1-[(2,3,6-trihydroxy-3-trifluoroacetamido-α-L-lyxo-hexopyranose)methyl]-anthracene-9,10-dione was obtained. HR-MS gave 451.1604 (calc for $C_{23}H_{24}F_3NO_5=451.1606$); NMR gave $C_6$ protons 1.25(d) and 1.14(d), $J_{5,6}=6.0$.

EXAMPLE 9

Preparation of 1-[(2,3,6-trideoxy-4-O-p-nitrobenzoyl-3-trifluoroacetamido-α-L-lyxo-hexopyranoyl)methyl-9,10-anthraquinone A. Twenty-five mg (0.042 mmoles) of the product of Example 8, paragraph A and 25 mg (0.247 mmoles) triethyl amine were mixed in 5 ml toluene and the mixture was stirred for 4 hr at 80°–88° C. The solution was evaporated to dryness. The residue was taken up in 10 ml toluene and again evaporated to dryness. The residue was dissolved in 3 ml MeOH and water added to the cloud point (~3 ml). The mixture was heated to clear solution and then chilled overnight. The solid was filtered to give 20 mg (80%) 1-[(2,3,6-trideoxy-4-O-e-nitrobenzoyl-3-trifluoro-acetamido-α-L-lyxo-hexopyranoyl)methyl-9,10-anthraquinone; mp 253°–256° C.

The mass spectrum gave m/e of 596 and analysis: $C_{30}H_{23}F_3N_2O_8 \cdot 0.5H_2O$ was as follows: C 59.51; H 3.99; N 4.63; (calc); C 59.56; H 3.84; N 4.60; (found).

B. In an analogous manner, 1-[(2,3,6-trideoxy-3-trifluoroacetamido-α-L-lyxo-hexopyranosy)methyl]-9,10-anthraquinone was prepared using the product of Example 8, paragraph B. The desired anthraquinone, formed in 71% yield had an mp 288°–292° C., a mass spectrum m/e=447;

analysis $C_{23}H_{20}F_3NO_5$ gave C 61.74; H 4.51; N 3.13 (calc); C 61.91; H 4.79; N 3.18 (found).

NMR (90 MHz) $C_6$ proton 1.23(d); $J_{5,6}$ 6.6 Hz, linker $CH_2$ 3.69(d).

EXAMPLE 10

Removal of TFA

The TFA was removed from the product of Example 9, paragraph B to give 1-[(2,3,6-trideoxy-3-amino-α-L-lyxo-hexopyranosyl)methyl]-9,10-anthraquinone as follows: 50 mg (0.112 mmoles) of 1-[(2,3,6-trideoxy-3-trifluoro acetamido-α-L-lyxo-hexopyranosyl)methyl]-9,10-anthraquinone were mixed with 1 ml N butyl amine in 15 ml MeOH.

The mixture was refluxed for 3 days, and the reaction followed by TLC. Starting material has $R_f 0.9$ and product has $R_f 0.4$. The solution was evaporated to dryness. The residue wwas purified on thick silica gel plate, developed with 25% MeOH/CHCl₃. The eluted product was dissolved in 3 ml MeOH and 1 ml CCl₄ (hot) filtered, and then chilled. A gel formed and was slowly filtered until the gel dried on the filter to give 17 mg (44%) of 1-[(2,3,6-trideoxy-3-amino-α-L-lyxo-hexopyranosyl)methyl]-9,10-anthraquinone mp>280° C. #C-18 HPLC 0.1N NaH₂PO₄/CH₃CN showed 100% of one peak.

We claim:

1. A method of preparing derivatives of a 2-deoxyhexopyranose having a pentadienyl substituent in place of OH at C-1 which comprises treating 1-position-activated-2-deoxyhexopyranose, with a 1-trimethylsilyl-2,4-pentadiene compound in a reaction mixture which includes a Lewis acid.

2. The method of claim 1 wherein the 1-position-activated 2-deoxyhexopyranose has a O-p-nitrobenzoyl group at the 1-position.

3. The method of claim 1 wherein the 1-position-activated 2-deoxyhexopyranose is a 1-O-p-nitrobenzoyl derivative of daunosamine.

4. The method of claim 3 wherein the 1-position-activated 2-deoxyhexopyranose is 1,4-di-O-p-nitrobenzoyl-2,3,6-trideoxy-3-trifluoroacetamido-α-L-lyxohexopyranose.

5. A method for preparing a compound of the formula:

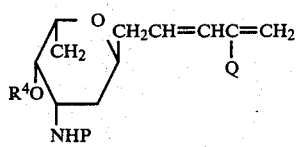

wherein

Q is H, $CH_3$, $OCH_3$, $OCH_2CH_3$, $OCH_2CH_2OCH_3$, or O-tetrahydropyranyl;

$R^4$ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro; and P is a protecting group selected from the group consisting of acetyl, trichloroacetyl and trifluoroacetyl;

which method comprises treating a compound of the formula:

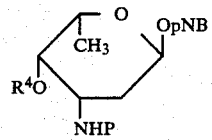

wherein $R^4$ and P are as above-defined and pNB is p-nitrobenzoyl, with a compound of the formula

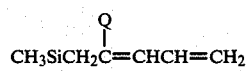

where Q is as above defined, in a reaction mixture which includes a Lewis acid.

6. A method for preparing a 2-deoxyhexopyranosyl acetaldehyde which comprises treating a 1-position-activated 2-deoxyhexopyranose with 1-trimethylsilyl-2-propene in a reaction mixture which includes a Lewis acid, to obtain a C.1 allyl intermediate, followed by treating said intermediate with ozone.

7. The method of claim 6 wherein the 1-position-activated 2-deoxyhexopyranose has a O-p-nitrobenzoly group in the 1-position.

8. The method of claim 6 wherein the 1-position-activated 2-deoxyhexopyranose is a 1-O-p-nitrobenzoyl derivative of daunosamine.

9. The method of claim 8 wherein the 1-position-activated 2-deoxyhexopyranose is 1,4-di-O-p-nitrobenzoyl-2,3,6-trideoxy-3-trifluoroacetamido-α-L-lyxohexopyranose.

10. A compound of the formula

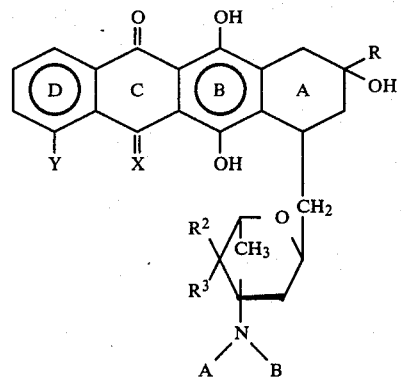

wherein

X is O or NH;

Y is H or $OCH_3$; with the proviso that if X=NH, Y must be $OCH_3$;

R is $COCH_3$, $COCH_2OH$, $CHOHCH_3$, $CHOHCH_2OH$, H, 1–3C alkyl, 1–2C terminal hydroxylkyl or the 2–7C alkyl or aryl organic acid esters or 1–6C alkyl ethers thereof;

at least one of $R^2$ and $R^3$ is H, and the other is OH or $OCH_3$; and

A and B is each independently H or alkyl (1–6C), or A and B taken together are morpholino thiomorpholino, or piperidinyl, unsubstituted or mono- or di-substituted by CN.

11. A compound of the formula

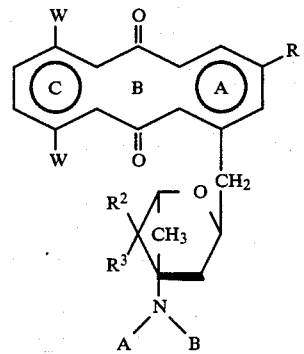

wherein

W is H or OH;

R is $COCH_3$, $COCH_2OH$, $CHOHCH_3$, $CHOHCH_2OH$, H, 1–3C alkyl, 1–2C terminal hydroxyalkyl or the 2–7C alkyl or aryl organic acid esters or 1–6C alkyl ethers thereof;

at least one of $R^2$ and $R^3$ is H, and the other is OH or $OCH_3$; and

A and B is each independently H or alkyl (1–6C), or A and B taken together are morpholino, thiomorpholino, or piperidinyl, unsubstituted or mono- or di-substituted by CN.

12. A compound of the formula

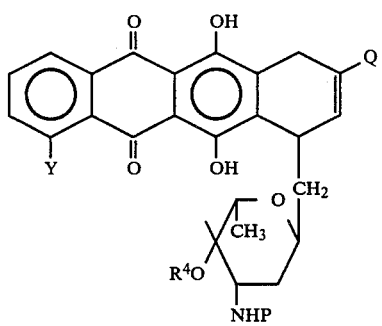

wherein
Y is H or OCH₃;
R⁴ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro;
P is a protecting group selected from the group consisting of acetyl, trichloroacetyl and trifluoroacetyl; and
Q is H, alkyl (1–3C), OCH₃, OCH₂CH₃, OCH₂CH₂OCH₃, O-tetrahydropyranyl, Br or COOCH₃.

13. A compound of the formula

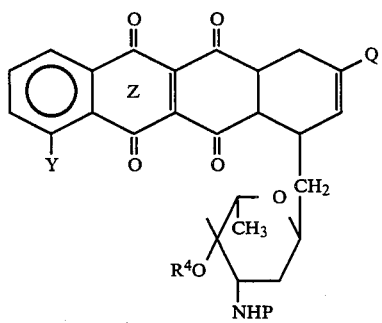

wherein
Y is H or OCH₃;
Z is a π bond or epoxide;
R⁴ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro;
P is a protecting group selected from the group consisting of acetyl, trichloroacetyl and trifluoroacetyl; and
Q is H, alkyl (1–3C), OCH₃, OCH₂CH₃, OCH₂CH₂OCH₃, O-tetrahydropyranyl, Br, or COOCH₃.

14. A compound of the formula

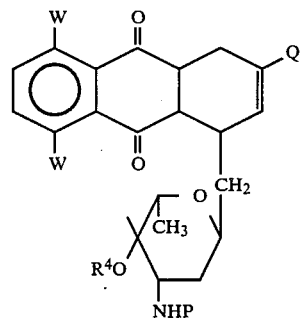

wherein
W is H or OH;
R⁴ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro;
P is a protecting group selected from the group consisting of acetyl, trichloroacetyl and trifluoroacetyl; and
Q is H, alkyl (1–3C), OCH₃, OCH₂CH₃, OCH₂CH₂OCH₃, O-tetrahydropyranyl, Br, or COOCH₃.

15. A compound of the formula
wherein
R⁴ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro;
P is a protecting group selected from the group consisting of acetyl, trichloroacetyl and trifluoroacetyl; and
Q is H, alkyl (1–3C), OCH₃, OCH₂CH₃, OCH₂CH₂OCH₃, O-tetrahydropyranyl, Br, or COOCH₃.

16. A compound of the formula

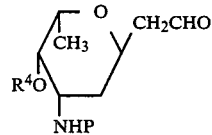

wherein
R⁴ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro; and
P is a protecting group selected from the group consisting of acetyl, trichloroacetyl and trifluoroacetyl.

17. A compound of the formula

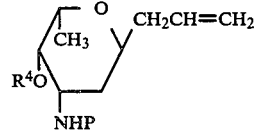

wherein
R⁴ is H, acyl (1–4C), unsubstituted aroyl (6–15C), or aroyl (6–15C) substituted on the benzene ring thereof by at least one substituent selected from the group consisting of hydroxy, alkoxy (1–4C), carbalkoxy (1–4C), halo, alkyl (1–4C) and nitro; and
P is a protecting group selected from the group consisting of acetyl, trichloroacetyl and trifluoroacetyl.

* * * * *